United States Patent [19]

De Feo et al.

[11] 4,011,224
[45] Mar. 8, 1977

[54] PROCESS FOR THE PREPARATION OF 7-OXO-7H-DIBENZO-[d e,h]-QUINOLIN-2-OL

[75] Inventors: Francesco De Feo, Milan; Franco Gonzati, Saronno (Varese); Alberto Osti, Milan, all of Italy

[73] Assignee: Aziende Colori Nazionali Affini ACNA S.p.A., Milan, Italy

[22] Filed: Dec. 26, 1974

[21] Appl. No.: 536,591

[30] Foreign Application Priority Data

Jan. 21, 1974 Italy .................................. 19614/74
July 16, 1974 Italy .................................. 25196/74

[52] U.S. Cl. .................................................. 260/278
[51] Int. Cl.² .......................................... C09B 5/14
[58] Field of Search ................................ 260/278

[56] References Cited

UNITED STATES PATENTS

3,912,739  10/1975  Boffa et al. ..................... 260/278

Primary Examiner—Paul M. Coughlan, Jr.
Attorney, Agent, or Firm—Hubbell, Cohen, Stiefel & Gross

[57] ABSTRACT

7-oxo-7H-dibenzo-[d e,h]-quinolin-2-ol which is useful as an intermediate in the preparation of dyestuffs is prepared by cycloisomerizing the novel compound, N-phenylacetyl phthalimide in an inert solvent and in the presence of a Friedel-Crafts catalyst to form the novel compound O-(3-hydroxy-1-isoquinolinyl)-benzoic acid which is then cyclized by dehydrating condensation to form the 7-oxo-7H-dibenzo-[d e,h]-quinolin-2-ol.

16 Claims, 3 Drawing Figures

PROCESS FOR THE PREPARATION OF 7-OXO-7H-DIBENZO-[d e,h]-QUINOLIN-2-OL

BACKGROUND OF THE INVENTION

Field of the Invention

The present invention relates to a process for the preparation of 7-oxo-7H-dibenzo-[d e,h]-quinolin-2-ol (I), a known compound also known as 1-aza-2-hydroxy-benzanthrone.

Prior Art

The known compound, 1-aza-2-hydroxy-benzanthrone (I) is a useful intermediate for the synthesis of dyestuffs. Thus, for instance, starting from that compound, and by operating according to the procedures described in Italian Pat. Nos. 869,691 and 901,929, excellent vat dyes are obtained, these dyes having color hues ranging from brilliant blue to violet blue. These dyes belong to a new series of dyes based on 5,14-diaza-isoviolanthrone, which is structurally similar to isoviolanthrone but which have application characteristics, which for purity of tone are much superior, particularly for the exceptional chlorine resistance.

Compound (I), i.e., 1-aza-2-hydroxy-benzanthrone, may also be used in the preparation of azoic dyes, since it is able to couple in the 3-position ortho with respect to the OH group.

Italian Patent No. 860,016, discloses a method for the preparation of 7-oxo-7H-dibenzo[d e,h]-quinolin-2-ol by reacting 1,4-naphthoquinone and methyl hexadienoate, to form the intermediate adduct, methyl 1,1a,4,4a-tetrahydro-anthraquinone)-acetate, which, after treatment with ammonia and subsequent dehydrogenation and cyclization in the presence of air and KOH, leads to compound (I).

Italian Patent Application 26722 A/73, by Montedison S.p.A., filed on July 18, 1973 discloses a process for the preparation of compound (I) wherein an alkyl ester of anthraquinone-1-acetic acid is directly reacted with ammonia in hydroxylated solvents, preferably methanol, in the presence of a strong base and/or a reducing agent according to the reaction scheme:

wherein R is an alkyl group having from 1 to 5 carbon atoms. These known techniques are not, however, related to the process of the present invention.

SUMMARY OF THE INVENTION

It is an object of the invention to provide new processes for the production of 1-aza-2-hydroxy-benzanthrone (I) and in accordance with the invention, such new processes are provided. In addition, the invention also provides new compounds which, among other things, are intermediates in the production of (I).

According to the process of the invention, 1-aza-2-hydroxy-benzanthrone (I), is prepared by cycloisomerizing phenyl-acetylphthalimide (II) in the presence of a Friedel-Crafts type catalyst (see G.A. Olah: "Friedel-Crafts and Related Reactions", ed. 1964 Interscience Publishers, pages 201–298; also see: C.A. Thomas: "Anhydrous Aluminum Chloride in Organic Chemistry", ed. 1941, Reinhold Publishing Corp.), in an inert solvent reaction medium having a sufficiently high boiling point to obtain the novel intermediate, -(3-hydroxy-1-isoquinolinyl)-benzoic acid (III). This compound (III) is cyclized with concentrated $H_2SO_4$ to form the desired 1-aza-2-hydroxy-benzanthrone compound by dehydrating condensation thereof. The Friedel-Crafts type catalysts that may be employed include $AlCl_3$, $BF_3$, $TiCl_3$, etc. $AlCl_3$ is however, the preferred catalyst.

The various reaction steps are shown in the following scheme:

(III)

(I)

The new method for preparing 1-aza-2-hydroxy-benzanthrone (I) involves the preparation of two new intermediate compounds, i.e.:

a. N-phenyl-acetyl-phthalimide (II) and
b. -(3-hydroxy-1-isoquinolinyl)-benzoic acid (III).

Both of these intermediate compounds may be usefully employed "per se" in industry and thus are part of the invention.

In fact, compound (II) may, for instance, be used as an activator of persalts in bleaching agents of the peroxide type, while compound (III), may be used, for instance, as a coupling material in the preparation of azoic dyes.

According to a further aspect of the invention, N-phenyl-acetyl-phthalimide (II) is prepared by reacting potassium-phthalimide with phenylacetyl chloride in an inert solvent, at a temperature between room temperature and 150° C., preferably between 30° and 130° C.

Among the inert solvents that may be used in the process, there are included, aromatic or aliphatic, chlorinated or nonchlorinated hydrocarbons such as benzene, toluene, monochlorobenzene, dichlorobenzenes, trichlorobenzenes, tetrachloroethane, carbon tetrachloride, dichloroethane, nitrobenzene, nitroalkanes, etc. After the reaction is complete, the product is separated according to known techniques.

Alternatively, N-phenyl-acetylphthalimide (II) is prepared by condensation of phthalimide (with the imido hydrogen being un-substituted) with phenylacetylchloride, in a reaction medium consisting of an aprotic, polar organic solvent which is completely soluble in water in any ratios in the presence of a tertiary amine as a neutralizer for the hydrochloric acid which is formed during the reaction, and at a reaction temperature between 0° and 90° C., preferably between 15° and 50° C.

In this latter alternative, the aprotic polar organic solvents that may be used include dialkylamides or alkyl lactams of the following formulae:

(IV)         (V)

wherein R is hydrogen or a lower alkyl having from 1 to 3 carbon atoms;

R' and R'' are independently selected from the group consisting of lower alkyl groups having from 1 to 3 carbon atoms;

$R_1$ is a lower alkyl group having from 1 to 3 carbon atoms; and

$R_2$ is an alkylene group having from 3 to 6 carbon atoms.

Preferred examples of such solvents are dimethyl formamide, diethyl formamide and N-methyl-pyrrolidone.

Among the tertiary amines, which are used for neutralizing the formed hydrochloric acid there are inclined trialkylamines, the alkyl radicals of which have from 1 to 4 carbon atoms, such as, trimethylamine, triethylamine and tripropylamine; heterocyclic amines such as pyridine, picoline, quinoline and lutidine and alicyclic amines in which the alkyl radicals have from 1 to 3 carbon atoms, such as, N-methyl- and N-ethyl-piperidine, N-methyl and N-ethyl-morpholine or N,N'-diethyl-piperazine.

The preferred tertiary amines are triethylamine and pyridine.

The reaction, according to this latter alternative, may be represented by the following scheme wherein $R_3N$ is the tertiary amine:

The results obtained using this alternative method of preparing N-phenylacetyl-phthalimide are quite unexpected inasmuch as the heretofore tried methods of synthesizing this compound had given either negative or unsatisfactory results.

Thus, for example, by reacting phenylacetylchloride with potassium phthalimide in dimethyl formamide, there was obtained a product that was contaminated by many impurities.

Also, when reacting phthaloylchloride with phenacetylamide in toluene, one obtains a practically useless product, because it is contaminated by large amounts of by-products and impurities.

In comparison with the first alternative of the preparation method for N-phenylacetylphthalimide as described above and which uses an alkalimetalphthalimide as the starting material, this second alternative offers operational advantages.

The cycloisomerization to o-(3-hydroxy-1-isoquinolinyl)-benzoic acid (III) is carried out in an inert solvent in the presence of a Friedel-Crafts catalyst, at a temperature between 50° and 200° C., preferably between 60° and 170° C., by adding the catalyst either on a previously prepared dispersion of N-phenylacetylphthalimide in the inert solvent, or directly onto the reaction mass itself by operating in one single reactor and in one single processing step.

Among the inert solvents used for carrying out the cycloisomerization step there may be included the conventional solvents usually employed in connection with the Friedel-Crafts catalysts (see G.A. Olah, supra, pages 298/304), provided that they have boiling points within the range of temperatures chosen for the reaction and which will not compete with the desired product in the reaction.

Among the various solvents satisfying the above indicated requirements, particularly suited solvents are the aromatic and aliphatic chlorinated hydrocarbons such as chlorobenzene, dichlorobenzenes, trichlorobenzenes and tetrachloroethane.

Thus, in the case in which the reactions for the preparation of N-phenyl-acetyl-phthalimide and for the cycloisomerization to o-(3-hydroxy-isoquinolinyl)-benzoic acid starting from potassium phthalimide are carried out in a single step and in a single reactor, obviously it will be necessary to use, from the very beginning, an inert solvent of the type specified in the preceding two paragraphs.

The molar ratio between the Friedel-Crafts catalyst and the N-phenyl-acetyl-phthalimide, may vary from 2-5:1, with the most advantageous results being obtained with a molar ratio equal to or very near 2:1.

The subsequent cyclocondensation reaction of the o-(3-hydroxy-1-isoquinolinyl)-benzoic acid (III) to 7-oxo-7-H-dibenzo-[d e,h]-quinolin-2-ol (I) is conducted with condensation agents of the dehydrating type, such as, for instance, concentrated $H_2SO_4$, oleum, polyphosphoric acids, sulphuric or phosphoric anhydrides for 0.5–3 hours at a temperature between 90° and 200° C., or by melting at 110°–250° C. with the double salt $AlCl_3.NaCl$.

DESCRIPTION OF THE PREFERRED EMBODIMENTS

The invention will now be described in greater detail in the following examples which are intended to illustrate the invention without however limiting it.

EXAMPLE 1

Preparation of N-phenylacetylphthalimide 148 g of potassium phthalimide were dispersed in 500 ml. of technical dichlorobenzene. Into this dispersion, a solution of 133 g. of phenylacetylchloride in 100 ml. of dichlorobenzene was slowly poured, at room temperature.

Figure 1:
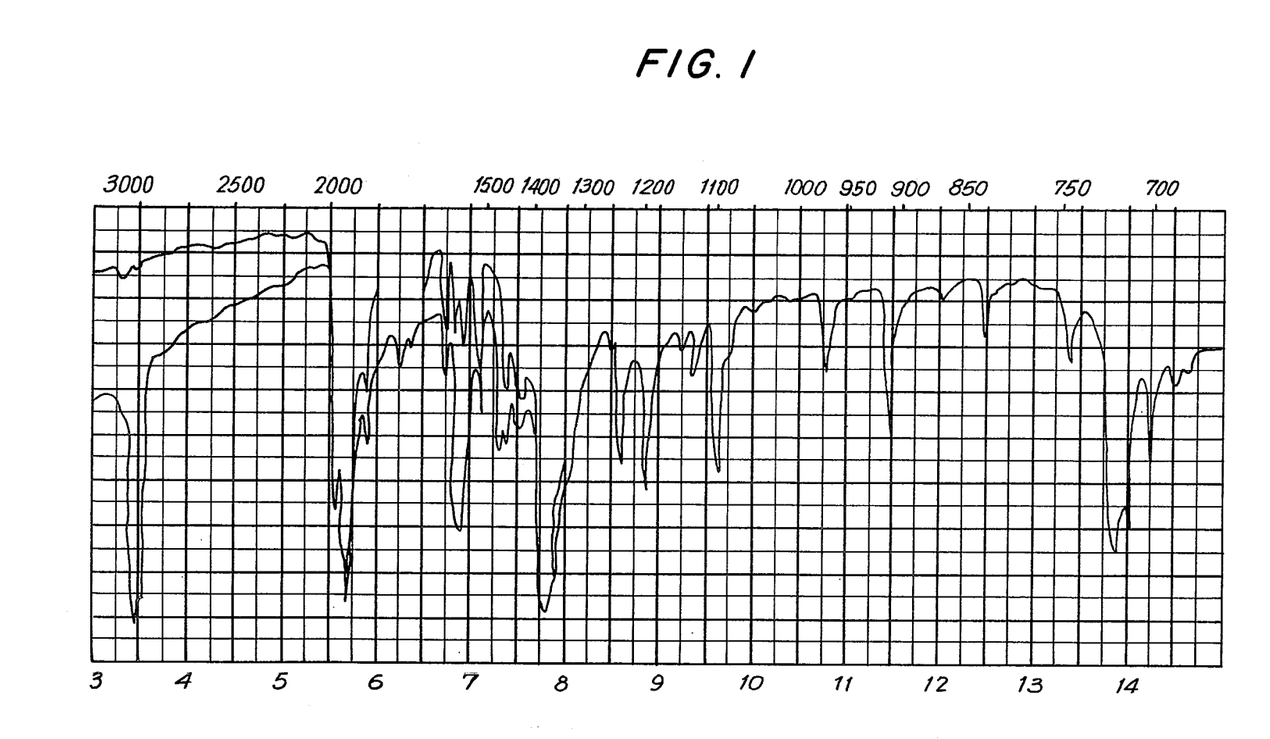
FIG. 1 is an IR spectrum of the product of Example 1.

The reaction mass was then heated to 120° C. and maintained at this temperature for about 8 hours with stirring. Thereafter, the reaction mass was cooled to room temperature, and filtered under vacuum, by thoroughly squeezing out the filter cake. The filter cake was dispersed in water with stirring and then filtered again under vacuum. The product thus obtained was dried overnight in an oven at 80° C. to thereby obtain 106 g. of N-phenylacetylphthalimide in the form of a white-yellowish powder having a m.p. of 150°–5° C., and having an infrared absorption spectrum as shown in FIG. 1.

EXAMPLE 2

Preparation of N-phenylacetylphthalimide

Into a dispersion of 148 g. of potassium phthalimide in 1500 ml. of dichloroethane there was dripped over a 15 minute period at room temperature, a solution of 125 g. of phenylacetylchloride in 100 ml. of dichloroethane. The resulting mixture was then heated to 40° C. for 2 hours, and thereafter filtered under vacuum by washing the potassium chloride cake with a total of 200 ml of dichloroethane.

The filtrate and the washings were combined and then subjected to steam distillation in order to eliminate the solvent which was recovered after stratification of the distillate.

The mass from which the solvent had been removed was then cooled to room temperature under stirring. The N-phenacetylphthalimide separated in the form of granules having a straw-yellow color were filtered under vacuum and finally washed with water.

After drying overnight at 80° C., there were obtained 170 g. of product having a m.p. of 147°–149° C. and showing an infrared absorption spectrum identical with that of the product obtained in Example 1.

EXAMPLE 3

Preparation of N-phenylacetylphthalimide

Into a 2 liter reactor there were placed 800 g. of dimethylformamide, 170 g. of triethylamine and 206 g. of phthalimide. Into the resulting suspension, under vigorous stirring, and over about 1 hour, 226 g. of phenylacetylchloride were slowly dripped in, while the reactor was cooled by an outside water bath, in order to prevent the temperature from exceeding 25°–30° C.

The reaction mass was kept under stirring for 5 hours at 25°–30° C., and was then discharged into a beaker containing 8 liters of water. The mass was then subjected to vigorous stirring for about a further 30 minutes at room temperature, and thereafter filtered under vacuum.

From the filtrate, the dimethylformamide was recovered by fractional distillation. The cake was then washed four times with a total of 4 liters of water, and thereafter it was dried overnight at 70°–80° C. Thereby, 318 g. of dry product having a m.p. of 135°–145° C. and a yellow-orange hue were obtained. By crystallization from ethanol there was obtained a yellow product having a m.p. of 152°–154° C.

The following are the elemental analysis data of this material:

|  | C% | H% | N% |
| --- | --- | --- | --- |
| Found value | 72.20 | 4.30 | 5.55 |
| Theoretical value | 72.50 | 4.18 | 5.10 |

The spectral characteristics of the material are the same as those of the product described in Example 1.

EXAMPLE 4

Preparation of o-(3-hydroxy-1-isoquinolinyl)-benzoic acid 148 g. of N-phenylacetylphthalimide were dispersed in 2600 ml. of technical dichlorobenzene. This dispersion was then heated to 120° C. with stirring, after which the heads were distilled off under slight vacuum to dehydrate the solvent. Thereafter, the dispersion was cooled to about 70° C. and then 157 g. of anhydrous $AlCl_3$ powder were added thereto.

The reaction mass was then heated to 150° C. and maintained at this temperature for 6 hours with stirring.

The reaction mass was then cooled to about 80° C. and 2600 ml. of water were poured onto it in order to decompose the aluminum complex. The mass was then maintained, under stirring and without heating for one night and the dichlorobenzene was then steam distilled. The aqueous dispersion was then filtered and the cake was washed with water. The cake was dispersed in a solution of 30 ml. of 36° Be NaOH in 2500 ml. of water, and was kept under stirring for 15 minutes at room temperature; finally it was filtered and the precipitate was washed with water.

The filtrate was acidified with acetic acid to a pH of 3–3.5, and then the obtained yellow filtrate was filtered and washed with water up to a neutral pH.

The filtrate was dried overnight at 80° C. and 74 g. of a yellow product having a m.p. of 245°–250° C. (with apparent decomposition) were obtained.

Figure 2:
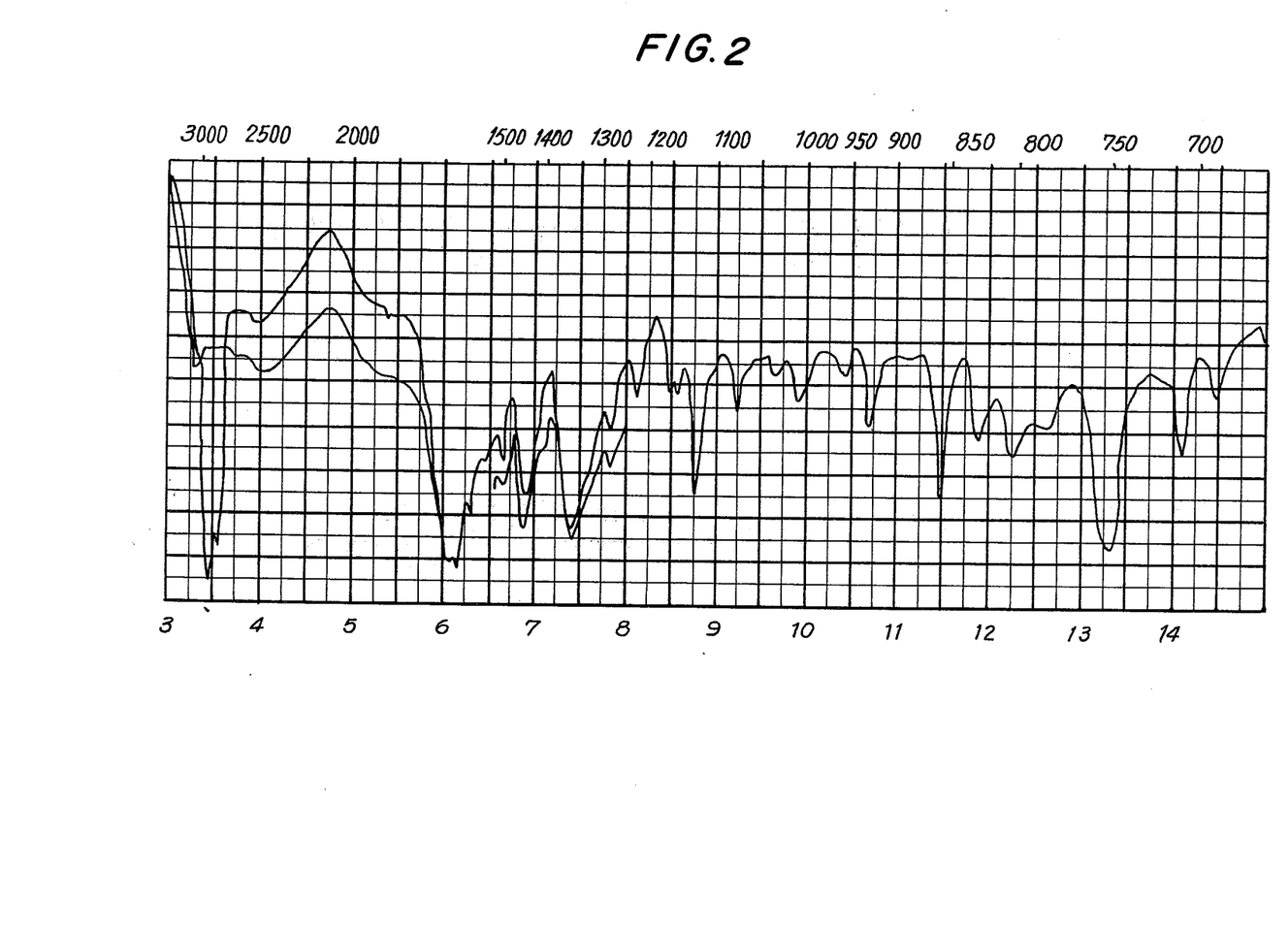
FIG. 2 is an IR spectrum of the product of Example 4.

The equivalent weight as measured by the potentiometric method amounted to 260 (the theoretical equivalent weight being 265), and the product had an infrared absorption spectrum as shown in FIG. 2.

The obtained product was a statistical mixture of the enol and keto forms.

EXAMPLE 5

Single Step Preparation of o-(3-hydroxy-1-isoquinolinyl)-benzoic acid

Into a 250 ml. reactor, 90 ml of monochlorobenzene and 9.3 g. of potassium phthalimide were placed, with vigorous stirring.

To this mixture there was slowly admixed a solution of 8 g. of phenylacetylchloride in 10 ml. of monochlorobenzene.

The mixture was then kept under stirring for 2 hours at a temperature of 35°–40° C. The reaction mass was then diluted with 50 ml. of monochlorobenzene, after which 15 g. of anhydrous $AlCl_3$ powder were added thereto. The reaction mass was then heated to about 130° C. and maintained at that temperature for 5 hours. The mass was then subjected to stirring over night and the chlorobenzene was then steam distilled off. The mass was cooled and filtered and the filter cake was then washed with water.

The filter cake was then dispersed in 60 ml. of water with 4 ml. of 36° Be NaOH and then stirred for 15 minutes and finally filtered.

The filtrate was acidified to a pH of 3–3.5 with acetic acid. Thereafter the cake was filtered and washed with water and finally dried overnight at 80° C.

Thereby, 2.7 g of o-(3-hydroxy-isoquinolinyl)-benzoic acid were obtained. The product had the same characteristics as that of Example 4.

EXAMPLE 6

Preparation of 7-oxo-7H-dibenzo[d e,h]-quinolin-2-ol 103 g. of o-(3-hydroxy-1-isoquinolinyl)-benzoic acid were dispersed in 310 ml. of 96% $H_2SO_4$. This dispersion was then heated to 130° C. and kept under stirring at that temperature for one hour. The reaction mass was then cooled to about 90° C. and was then carefully poured into about 20 liters of hot water at 90°–95° C.

The reaction mass was then stirred for 1 hour while leaving it to cool down.

The reddish colored precipitate that was formed was filtered and washed with water until a neutral pH was reached. The filter cake was then dried overnight in an oven at 100° C.

Figure 3:
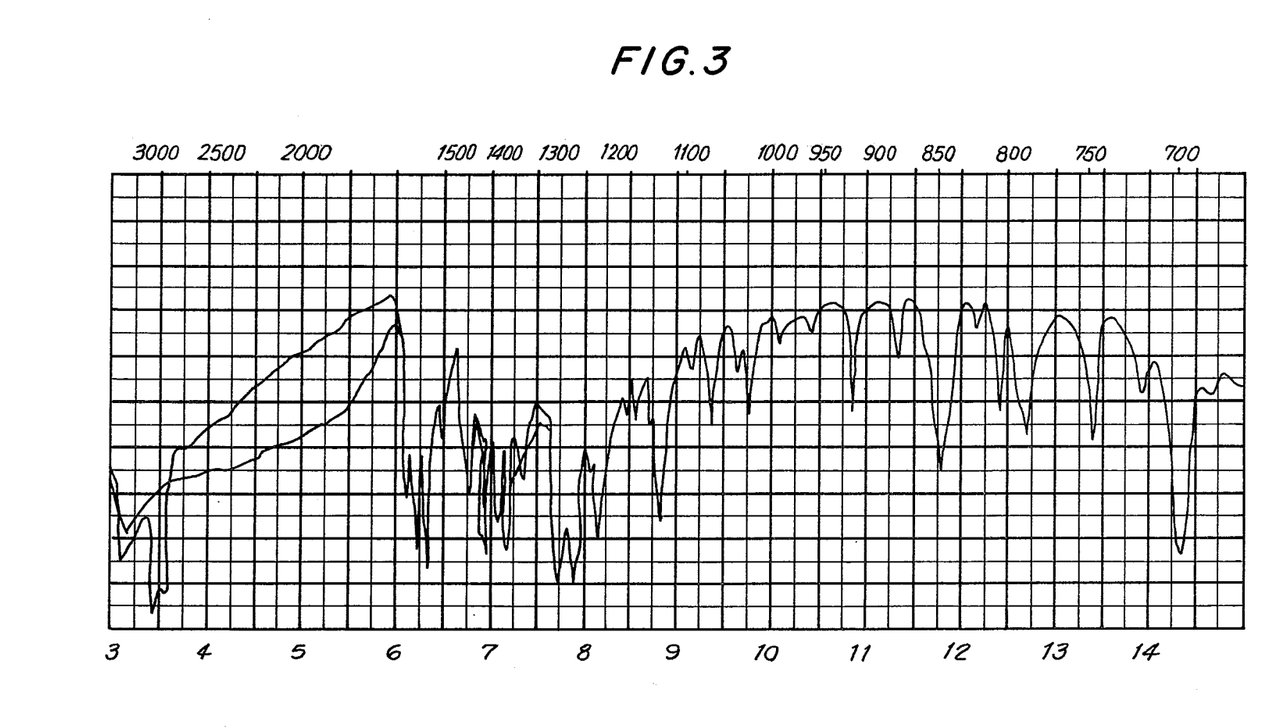
FIG. 3 is an IR spectrum of the product of Example 6.

56 g. of a product were thereby obtained, this product having the same chromatographic and spectral characteristics as those of the product described in Italian Pat. No. 860,016, mentioned above, and which had the infrared absorption spectrum shown in FIG. 3.

Variations and modifications can, of course, be made without departing from the spirit and scope of the invention.

Having thus described our invention, what we desire to secure by Letters Patent and hereby claim is:

1. A process for preparing 7-oxo-7H-dibenzo-[d e,h]-quinolin-2-ol, said process comprising cycloisomerizing N-phenyl-acetyl-phthalimide in an inert aliphatic or aromatic solvent, optionally substituted by chlorine or an $NO_2$ group and at a temperature of 50°–200° C. in the presence of $AlCl_3$ as a Friedel-Craft catalyst, the molar ratio of catalyst to N-phenyl-acetyl-phthalimide being 2–5:1 to form an intermediate which is o-(3-hydroxy-1-isoquinolinyl)-benzoic acid and thereafter subjecting the intermediate to dehydrating condensation to cyclize same and form 7-oxo-7H-dibenzo-[d e,h]-quinolin-2-ol.

2. A process according to claim 1, wherein the temperature is 60–170° C. and the molar ratio is about 2:1.

3. A process according to claim 1, wherein the N-phenyl-acetyl-phthalimide is obtained by reacting an alkali metal phthalimide with phenylacetylchloride in said at least one inert aliphatic or aromatic hydrocarbon solvent at a temperature between room temperature and 150° C.

4. A process according to claim 3, wherein said solvent is a chlorinated aliphatic or aromatic hydrocarbon and the reaction is effected at 30°–130° C.

5. A process according to claim 3, wherein the condensation and cycloisomerizing reactions are conducted sequentially in the same reaction zone in the presence of at least one inert chlorinated qromatic or aliphatic hydrocarbon.

6. A process according to claim 1, wherein the N-phenyl-acetyl-phthalimide is prepared by condensing phenylacetylchloride with phthalimide in a reaction medium consisting of a polar, aprotic solvent of the formulae:

$$R-\overset{O}{\underset{\|}{C}}-N\diagup^{R'}_{R''} \quad \text{or} \quad \diagup^{R_2}_{N}\diagdown_{R_1} C=O$$

(IV) (V)

wherein R is hydrogen, or a lower alkyl having from 1 to 3 carbon atoms;

R' and R" are independently selected from the group consisting of lower alkyl groups having from 1 to 3 carbon atoms, $R_1$ is a lower alkyl group having from 1 to 3 carbon atoms; and $R_2$ is an alkylene group having from 3 to 6 carbon atoms, in the presence of a tertiary amine, at a temperature between 0° to 90° C.

7. A process according to claim 6, wherein the temperature is between 15° and 50° C.

8. A process according to claim 6, wherein the tertiary amine is selcted from the group consisting of trialkylamines in which the alkyls have from 1 to 4 carbon atoms.

9. A process according to claim 8, wherein the trialkylamine is triethylamine.

10. A process according to claim 6, wherein the tertiary amine is selected from the group consisting of pyridine, quinoline, picoline and lutidine.

11. A process according to claim 10, wherein the tertiary amine is pyridine.

12. A process according to claim 6, wherein the tertiary amine is selected from the grup consisting of N-alkylpiperidines, N-alkylmorpholines and N,N'-dialkylpiperazines, wherein the alkyls have from 1 to 3 atoms.

13. A process according to claim 6, wherein the polar aprotic solvent is dimethylformamide.

14. A process according to claim 6, wherein the polar aprotic solvent is N-methyl-pyrrolidone.

15. A process according to claim 1, wherein the dehydrating condensation is effected in the presence of a dehydrating agent selected from the group consisting of concentrated $H_2SO_4$ optionally containing $SO_3$, polyphosphoric acids and phosphoric anhydride at a temperature between 90° and 200° C. for between 0.5 and about 3 hours.

16. A process according to claim 1, wherein dehydrating condensation is effected by melting the intermediate with the double salt $AlCl_3.NaCl$ at a temperature between 110° and 250° C.

* * * * *

UNITED STATES PATENT OFFICE
CERTIFICATE OF CORRECTION

Patent No. 4,011,224   Dated March 8, 1977

Inventor(s) Francesco De Feo et al.   Page 1 of 2

It is certified that error appears in the above-identified patent and that said Letters Patent are hereby corrected as shown below:

Column 1, line 24: "7-oxo-7H-dibenzo-[d e,h]-quinolin-2-01" should read -- 7-oxo-7H-dibenzo-[d e,h]-quinolin-2-ol --; line 48: "1,1a,4,4a-tetrahydro-anthraquinone)-acetate," should read -- 1-(1,1a,4,4a-tetrahydro-anthraquinone)-acetate, --.

Column 2, lines 44-45: "-(3-hydroxy-1-isoquinolinyl)-benzoic acid" should read -- o-(3-hydroxy-1-isoquinolinyl)-benzoic acid --.

Column 3, line 37: "b. -(3-hydroxy-1-isoquinolinyl)-benzoic acid" should read -- b. o-(3-hydroxy-1-isoquinolinyl)-benzoic acid --.

Column 4, lines 55-56: "inclined" should read -- included --.

Column 5, lines 38-39: "alkalimetalphthalimide" should read -- alkali metal phthalimide --.

UNITED STATES PATENT OFFICE
CERTIFICATE OF CORRECTION

Patent No. 4,011,224                       Dated March 8, 1977

Inventor(s) Francesco De Feo et al.        Page 2 of 2

It is certified that error appears in the above-identified patent and that said Letters Patent are hereby corrected as shown below:

Column 9, line 4 of claim 1: "aromatic solvent," should read -- aromatic hydrocarbon solvent, --; line 4 of claim 5: "qromatic" should read -- aromatic --.

Column 10, line 2 of claim 8: "selcted" should read -- selected --; line 2 of claim 12: "grup" should read -- group --; line 4 of claim 12: "1 to 3 atoms." should read -- 1 to 3 carbon atoms. --.

*Signed and Sealed this*

Twenty-fourth Day of May 1977

[SEAL]

Attest:

RUTH C. MASON
*Attesting Officer*

C. MARSHALL DANN
*Commissioner of Patents and Trademarks*